US008557600B2

(12) United States Patent
Mabuchi et al.

(10) Patent No.: US 8,557,600 B2
(45) Date of Patent: Oct. 15, 2013

(54) IMMUNOASSAY PRODUCT AND PROCESS

(75) Inventors: Masaharu Mabuchi, Beverly, MA (US); Hiroko Kimura, Yokohama (JP); Marc Emerick, Amesbury, MA (US); Phillip Clark, Wakefield, MA (US); Kurt Greenizen, Bradford, MA (US)

(73) Assignee: EMD Millipore Corporation, Billerica, MA (US)

( * ) Notice: Subject to any disclaimer, the term of this patent is extended or adjusted under 35 U.S.C. 154(b) by 313 days.

(21) Appl. No.: 11/582,727

(22) Filed: Oct. 18, 2006

(65) Prior Publication Data

US 2007/0243628 A1 Oct. 18, 2007

Related U.S. Application Data

(60) Provisional application No. 60/795,452, filed on Apr. 27, 2006, provisional application No. 60/732,994, filed on Nov. 3, 2005.

(51) Int. Cl.
*G01N 1/10* (2006.01)
(52) U.S. Cl.
USPC ............... 436/180; 422/63; 422/64; 422/65; 422/66; 422/67; 422/536; 435/7.9; 435/7.92
(58) Field of Classification Search
USPC ............. 422/101, 102, 104, 99, 63–67, 536; 435/7.9, 7.92; 436/538, 540, 542, 501, 436/504, 514, 180
See application file for complete search history.

(56) References Cited

U.S. PATENT DOCUMENTS

| 4,427,415 A | 1/1984 | Cleveland |
| 4,717,656 A | 1/1988 | Swanljung |

(Continued)

FOREIGN PATENT DOCUMENTS

| CN | 1328640 A | 12/2001 |
| EP | 0312394 A3 | 4/1989 |

(Continued)

OTHER PUBLICATIONS

Extended Europran Search Report received for EP Patent Application No. 09153124.4, mailed on Apr. 14, 2009, 6 pages.

(Continued)

*Primary Examiner* — Jyoti Nagpaul
(74) *Attorney, Agent, or Firm* — EMD Millipore Corporation

(57) ABSTRACT

A rapid, efficient and convenient method to detect one or more biological entities on a blotting membrane is provided. The detection can relate to the position, nature or amount of the biological substance on one or more membranes. The invention method involves a pressure assisted regiment (such as vacuum or positive gas pressure) for the supply and removal of reagents and permits washing of the contaminants from substances embedded in the membrane to be detected using very low volumes of liquid. This method enables completion of the blocking, washing and antibody binding steps in about 30 minutes without comprising blot quality. In another aspect, the invention is directed to an apparatus useful in conducting the method of the invention. The device is comprised of several layers including a porous support layer below the blotting membrane(s), a flow distributor above the blotting membrane(s) and a well on the flow distributor to contain the liquid to the desired area and to allow for lower starting volumes of such liquid. Preferably, the flow distributor is a non-binding or low binding hydrophilic porous membrane such as a 0.22 micron membrane.

5 Claims, 8 Drawing Sheets

(56) References Cited

U.S. PATENT DOCUMENTS

| | | | |
|---|---|---|---|
| 4,826,759 | A | 5/1989 | Guire et al. |
| 4,834,946 | A | 5/1989 | Levin |
| 4,948,442 | A | 8/1990 | Manns |
| 5,039,493 | A | 8/1991 | Oprandy |
| 5,108,704 | A | 4/1992 | Bowers et al. |
| 5,141,719 | A | 8/1992 | Fernwood et al. |
| 5,149,408 | A | 9/1992 | Perlman |
| 5,155,049 | A | 10/1992 | Kauvar et al. |
| 5,264,184 | A * | 11/1993 | Aysta et al. ............ 422/527 |
| 5,368,729 | A | 11/1994 | Stefkovich et al. |
| 6,303,389 | B1 | 10/2001 | Levin et al. |
| 6,395,504 | B1 | 5/2002 | Trudil |
| 6,656,428 | B1 | 12/2003 | Bickoff et al. |
| 2001/0001643 | A1 | 5/2001 | Simpson et al. |
| 2002/0187089 | A1 | 12/2002 | Baxbaun |
| 2003/0143124 | A1* | 7/2003 | Roberts et al. ........ 422/102 |
| 2004/0048392 | A1* | 3/2004 | Kidd .................... 436/178 |
| 2004/0245163 | A1 | 12/2004 | Lim et al. |
| 2004/0247490 | A1 | 12/2004 | Olivier et al. |
| 2007/0111325 | A1* | 5/2007 | Van Beuningen et al. .... 436/518 |
| 2007/0243628 | A1 | 10/2007 | Mabuchi et al. |

FOREIGN PATENT DOCUMENTS

| | | |
|---|---|---|
| EP | 1151794 B1 | 6/2006 |
| JP | 02-187110 | 7/1990 |
| JP | 2-187110 A | 7/1990 |
| JP | 4-227032 A | 8/1992 |
| WO | WO9216294 A1 | 10/1992 |
| WO | 00/20862 A1 | 4/2000 |
| WO | WO2004013607 A2 | 2/2004 |
| WO | WO2005003346 A1 | 1/2005 |

OTHER PUBLICATIONS

Biocompare Buyers Guide for Life Sciences, Empowering Expression Discoveries, RNA Quality? Unviased cDNA? qPCR?, www.biocompare.com, Apr. 14, 2011.

Product Review, "Snap i.d. Rapid Western blotting system", bitesizebio.com, Apr. 14, 2011.

U.S. Appl. No. 60/732,994, M. Mabuchi, et al.

European Search Report EP 1783494 A1.

European Search Report EP1783495 A1.

* cited by examiner

Example        Comparative Example

IMMUNOASSAY PRODUCT AND PROCESS

CROSS-REFERENCE TO RELATED APPLICATIONS

This application claims the benefit of U.S. Provisional Application No. 60/795,452, filed on Apr. 27, 2006 and U.S. Provisional Application No. 60/732,994, filed on Nov. 3, 2005.

The invention relates to a laboratory device and process of using the device to detect the position of or presence/absence of substances that are contained in a blotting membrane. More particularly, it concerns a technique for applying reagents and wash solutions to a blotting membrane to accomplish this detection quickly via the use of a vacuum or positive pressure.

BACKGROUND OF THE INVENTION

The use of gel electrophoresis is currently the ubiquitous technique for the separation of biological materials. (Nonbiological materials can also be separated using gels or other chromatographic supports as well, but the scope of effort with regard to biologicals is greater.) Typical applications include separation of nucleic acid fragments of various sizes either in the context of sequence determination; in the detection of polymorphisms; or verification of sizes in other contexts. Also frequently conducted are separations of proteins and glycoproteins and application of gel separations as verification of homogeneity or purity.

In all of these procedures, mixed samples of biological entities are applied to electrophoretic gels and the components are separated by application of an electric field across the gel. Regardless of the manner in which the gel is developed, the resulting pattern of migration of the substances contained in the sample must be detected in some manner.

To conduct this detection, typically the gel support is contacted with a blotting membrane to which the substances are transferred in the same pattern in which they appeared on the gel. The "spots" are then detected by, at a minimum, by blocking the membrane with a protein or detergent solution to reduce non-specific binding (which otherwise leads to a high level of noise and low level of detection). Typical blocking agents include casein, bovine serum albumin (BSA), non-fat dry milk (generally about 1%) in a TBS-T or PBS-T solution. The biological entity is then incubated with an antibody specific for the antigen on the membrane. The membrane is then extensively washed to remove any contaminants (such as gel residues), unbound blocking proteins or antibodies and the like. The membrane is then treated and incubated with a secondary enzyme-, radioisotope-, fluorfluor-, or biotin-conjugated antibody specific for the primary antibody. The membrane is then extensively washed again to remove any unbound secondary antibody. Then a detector reagent, generally a chromogenic, chemiluminescent, fluorescent, radiological, or streptavidin-labeled material, is applied which either binds to, or is a substrate of the enzyme-conjugate. Lastly, the appropriate detection device is used to determine the presence, absence, position, quantity, etc of the biological entity. The last six steps generally take from 3-6 hours to overnight depending upon the speed of the reaction between the selected reagents, the membrane and the biological entity and the process requires multiple incubation periods of the membrane on a rocking platform. It is a lengthy process that most researchers dislike and which consumes (wastes) a large volume of reagents.

Some researchers have suggested the use of the capillary action of an absorbent material such as filter paper placed below the membrane to draw the remaining fluids through the membrane and improve the speed of the process especially the washing steps.

U.S. Pat. No. 5,155,049 mentions a system called the Hybrid-Ease™ hybridization chamber marketed by Hoefer Scientific Instruments. This chamber comprises two grids between which the membrane is sandwiched. The grid plates are snapped into position surrounding the membrane, and syringes fitted into the open space created by the grids. One syringe is used to apply reagents and wash, and the other to withdraw excess. The system requires large volumes of liquid in order to operate, is cumbersome to employ and is still quite time consuming. It also mentions that in some particular assays, such as ELISA assays, in small volume wells (such as 96 well microtiter plate), others have used vacuum to draw liquids through one or more membranes in a washing step. However, they discount this effort as it is only available in small volume applications and still is uncontrollable. They suggest instead that the better method is to use a manual press having the membrane on top of a filter paper and cover layer and then pressing the membrane sandwich between two plates to squeeze the liquid through the membrane and into the paper.

It is clear that a more efficient method for detection of the biological materials or entities on blotting membranes is required. The present invention permits a more effective and efficient detection of biological entities in a blotting membrane.

SUMMARY OF THE INVENTION

A rapid, efficient and convenient method to detect one or more biological entities on a blotting membrane is provided. The detection can relate to the position, nature or amount of the biological substance on one or more membranes. The invention method involves a pressure assisted regiment, selected from positive pressure or a vacuum assisted regiment for the supply and removal of reagents and permits washing of the contaminants from substances embedded in the membrane to be detected using very low volumes of liquid. This method enables completion of the blocking, washing and antibody binding steps in about 30-45 minutes without comprising blot quality.

Thus, in one aspect, the invention is directed to a method to pass liquid, such as an antibody solution, detection reagent or wash, through one or more membranes in which one or more biological substances to be detected are embedded. The membrane may, for example, correspond to the migration pattern of a sample subjected to separation on an electrophoresis gel. The membrane may also be a specific-binding assay solid support.

This method is particularly useful for membranes that are obtained by blotting of a gel support which has been used for electrophoretic separation of materials contained in a sample or verification of purity.

In another aspect, the invention is directed to an apparatus useful in conducting the method of the invention. The device is comprises of several layers including a porous support layer below the one or more layers of blotting membrane, a flow distributor above the blotting membrane(s) and a well on the flow distributor to contain the liquid to the desired area and to allow for lower starting volumes of such liquid. Preferably, the flow distributor is a non-binding or low binding porous membrane such as a 0.22 micron membrane.

The device has one or more blotting membranes mounted between the flow distributor and the support and is then placed on or into a vacuum manifold of suitable dimensions, or a pressure chamber is fit over the top of the flow distributor. The process is then run with the use of vacuum or positive pressure between the necessary steps to move the liquid through the membrane.

It is an object of the present invention to provide a device for conducting vacuum assisted immunoassays comprising a porous support, a flow distributor placed on top of the porous support and one or more reagent wells mounted on top of the flow distributor.

It is another object of the present invention to provide a device for conducting positive pressure assisted immunoassays comprising a porous support, a flow distributor placed on top of the porous support and one or more reagent wells mounted on top of the flow distributor.

It is another object of the present invention to provide a device for conducting vacuum assisted immunoassays comprising a vacuum manifold, porous support mounted on the vacuum manifold, a flow distributor placed on top of the porous support and one or more reagent wells mounted on top of the flow distributor.

It is a further object of the present invention to provide a device for conducting positive pressure assisted immunoassays comprising a manifold, porous support mounted on the manifold, one or more blotting membranes placed on the porous support, a flow distributor placed on top of the one or more porous membranes, one or more reagent wells mounted on top of the flow distributor and a positive pressure device removably mounted on top of the flow distributor.

It is a further object of the present invention to provide a process for conducting vacuum assisted immunoassays comprising the steps of:
a. providing a vacuum manifold, a porous support placed on the vacuum manifold, one or more membranes containing one or more biological entities to be assayed, the membrane being placed on the porous support, a flow distributor placed on top of the membrane and one or more wells placed on top of the flow distributor,
b. adding one or more reagents to the one or more wells and applying a vacuum to pull the reagents into the membrane, and
c. adding one or more washing agents to the one or more wells and applying a vacuum to pull the washing agents and any unbound reagents through the flow distributor, membrane and porous support and into the vacuum manifold.
d. repeating steps (b and c) one or more additional times as desired or required.

It is another object of the present invention to provide a process for conducting vacuum assisted immunoassays comprising the steps of:
a. providing a vacuum manifold, a porous support placed on the vacuum manifold, one or more membranes containing one or more biological entities to be assayed, the membrane being placed on the porous support, a flow distributor placed on top of the membrane and one or more wells placed on top of the flow distributor,
b. adding one or more reagents to the one or more wells and applying a vacuum to pull the reagents into the membrane,
c. adding one or more washing agents to the one or more wells and applying a vacuum to pull the washing agents and any unbound reagents through the flow distributor, membrane and porous support and into the vacuum manifold, and
d. repeating steps (b and c) one or more additional times.

It is an object of the present invention to provide a process of passing a wash or reagent-containing liquid through a blotting membrane containing one or more biological entities, at least one of which is to be detected wherein the process comprises:
a. providing a vacuum manifold, a porous support placed on the vacuum manifold, a flow distributor and one or more wells placed on top of the flow distributor,
b. placing the one or more blotting membranes containing the one or more biological entities on the porous support,
c. placing the flow distributor on top of the blotting membrane(s),
d. adding a liquid to the well of the flow distributor, and applying a vacuum to draw the liquid through the flow distributor, blotting membrane(s) and porous support into the manifold.

It is an object of the present invention to provide a process of passing a wash or reagent-containing liquid through one or more blotting membranes containing one or more biological entities, at least one of which is to be detected wherein the process comprises:
a. providing a manifold, a porous support placed on the manifold, a flow distributor and one or more wells placed on top of the flow distributor,
b. placing the one or more blotting membranes containing the one or more biological entities on the porous support,
c. placing the flow distributor on top of the blotting membrane(s),
d. adding a liquid to the well of the flow distributor, and applying a positive pressure to the flow distributor to move the liquid through the flow distributor, blotting membrane(s) and porous support to the manifold.

IN THE DRAWINGS

DETAILED DESCRIPTION OF THE INVENTION

Figure 1:
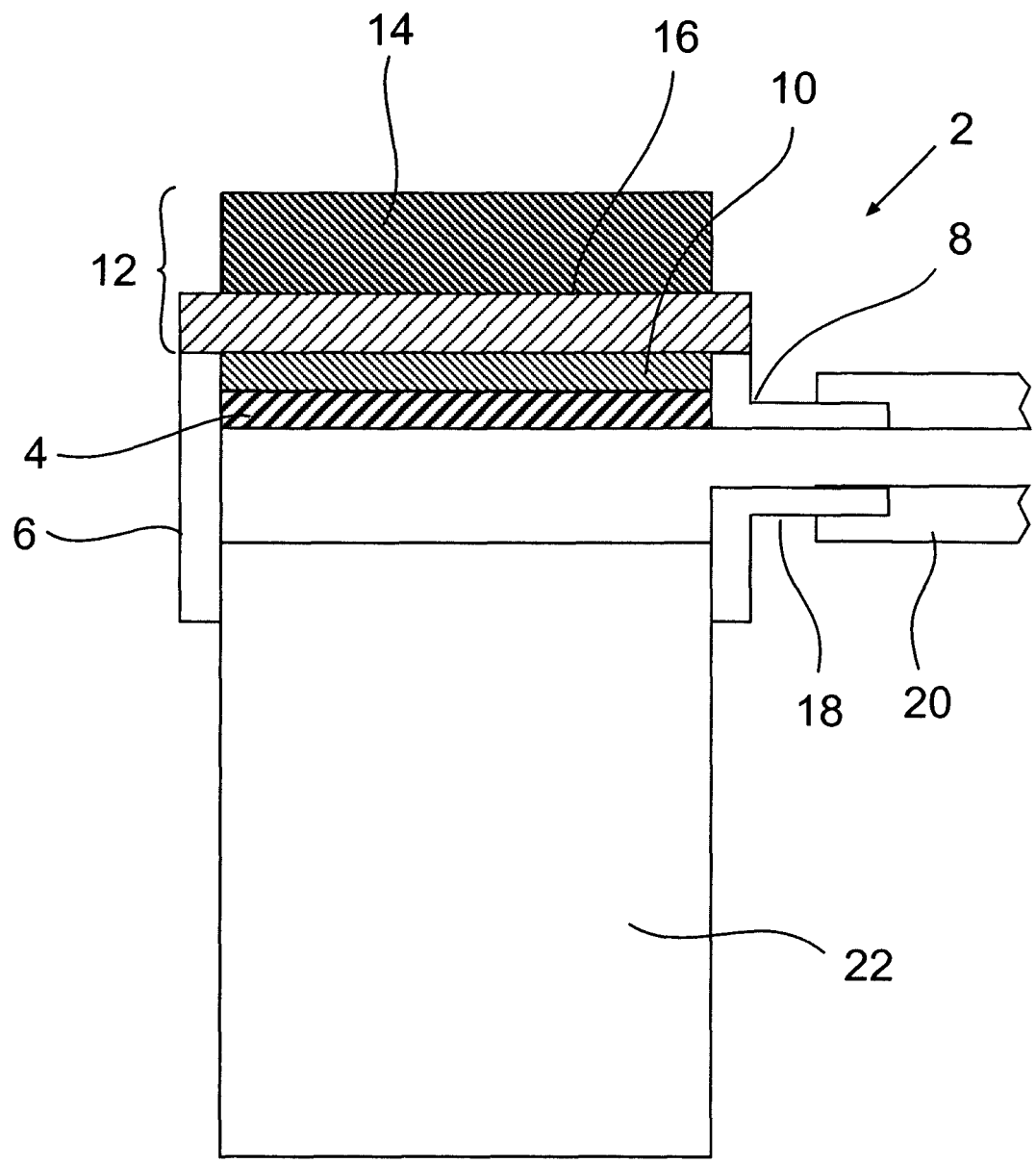
FIG. 1 shows a first embodiment of a device according to the present invention in cross-sectional view.

In order to accomplish the present invention a device according to the present invention is used. As shown in FIG. 1, the device 2 is comprised of a porous support 4. Preferably the support is formed with an edge 6 or mounting piece that is designed to fit into or onto a manifold 8 (described below). One or more layers of a blotting membrane 10 are placed on top of the support 4. A flow distributor 12 is then placed or mounted on top of the blotting membrane 10. The flow distributor may if desired either have one or more wells 14 (one shown in this embodiment) attached to the top surface 16 of the flow distributor 12 or it may be a separate piece (not shown) which is simply attached or placed on top of the flow distributor 12.

As shown in FIG. 1, the manifold 8 in this embodiment is a vacuum manifold which has a port 18 that is attached to a source of vacuum 20. Alternatively, positive pressure (to be described further below) can be used instead of a vacuum to drive the filtration/washing process. The port 18 is located below the porous support 4. A waste collection device 22, in this instance, a receptacle, is mounted below the manifold or if desired in the manifold (not shown) to collect the liquid pulled through the device 2. Alternatively, the waste collection device can be a waste drain or other similar device as is known to one of ordinary skill in the art.

Figure 2:
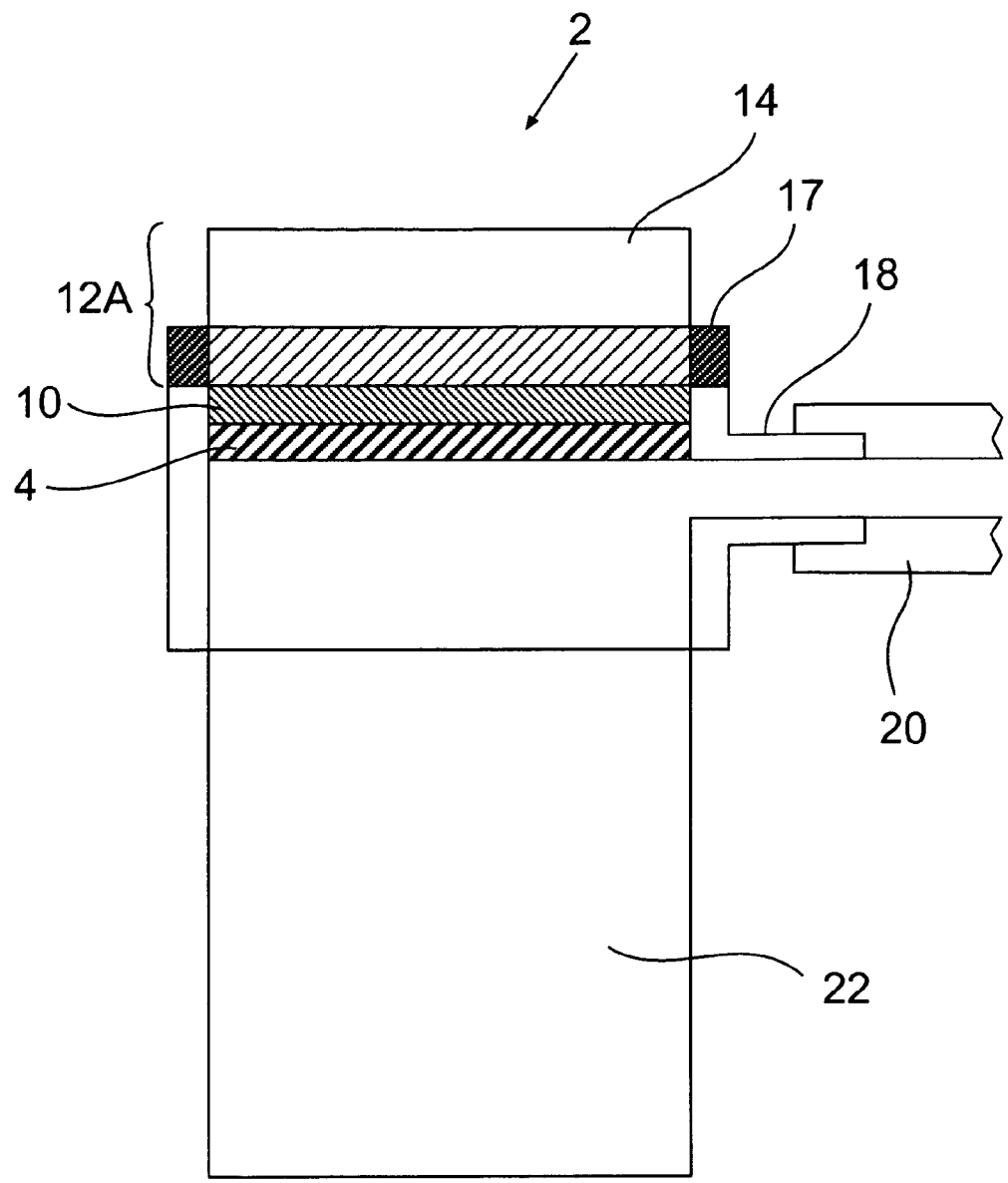
FIG. 2 shows a second embodiment of a device according to the present invention in cross-sectional view.

The flow distributor 12 is a porous structure. In one embodiment (shown) the entire structure is porous. In another embodiment shown in FIG. 2, the flow distributor 12A is only porous in the area 24 within the well(s) 14. The area 17 of the distributor 12 that is non-porous can be rendered so by filling the pores in that area 17 with a non-porous material such as a plastic or a glue, by collapsing the pores in that area 17 with heat and/or pressure and/or solvents as is well known in the art or by forming the distributor 12 to match the size of the outer dimension of the well(s) 14 and liquid tightly sealing the distributor 12 to the bottom of the well(s) 14 along its outer dimension.

The flow distributor 12 may be any porous structure that provides for even distribution of the liquid across its face and which is sufficiently porous to allow for easy movement under the influence of a vacuum and which is also capable of filtering out agglomerates, particles and other debris from the liquid.

The flow distributor may be of any desired size. Gels come in a variety of "standard" sizes from about 7 cm by 8 cm to a 20 cm by 20 cm area.

Such materials include but are not limited to woven, non-woven and fibrous porous filters such as TYVEK® or TYPAR® paper, cellulosic materials such as MIL-LISTAK+® filters available from Millipore Corporation of Billerica, Mass., membranes such as microporous membranes, sintered membranes such as POREX® filters and the like. Preferred are membranes, especially plastic microporous membranes.

A preferred pore size of such membranes is between about 0.1 and about 0.65 micrometer, preferably between 0.2 and about 0.45 micrometer and more preferably about 0.22 micrometer.

Additionally, the preferred filter or membrane has low binding characteristics for the reagents used in order to minimize the amount used. More preferably, as it is generally used with biological materials it is hydrophilic and has low protein binding characteristics. One such distributor is a hydrophilic DURAPORE® membrane formed of PVDF available from Millipore Corporation of Billerica, Mass. Another is a Millipore EXPRESS® hydrophilic PES membrane available from Millipore Corporation of Billerica, Mass.

The porous support 4 may be a simple screen, a grid, or a sintered porous structure such as a POREX® membrane or a coarse or large pored microporous filter, such as a non-woven paper polypropylene or polyethylene fabric or a 1-10 micron microporous filter. Such supports can be made of polymer, ceramic or metal materials including but not limited to metals, such as stainless steel, steel a steel alloy, aluminum and the like, and polymers such as polyethylene, polypropylene, polysulfones, styrenes, nylons and the like.

Figure 3:
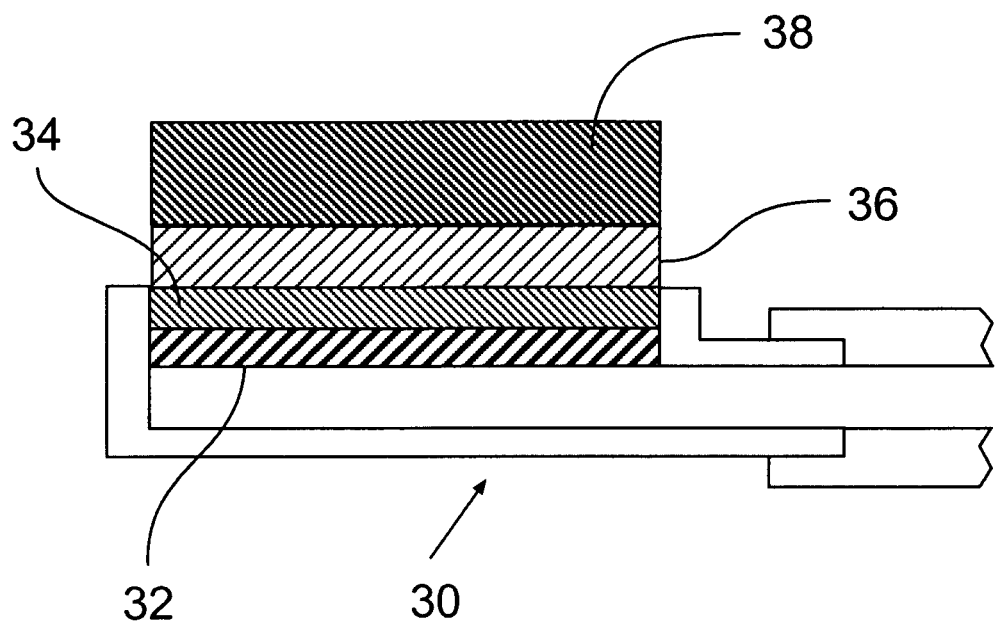
FIG. 3 shows a third embodiment of a device according to the present invention in cross-sectional view.

FIG. 3 shows an embodiment using a standard vacuum manifold 30. In this instance the manifold has porous support structure 32, such as a plastic or metal grid or a porous sintered sheet of plastic or metal or other similar devices as are well known in the vacuum art. The blotting membrane 34 is again placed on top of the support 32, covered by the flow distributor 36 and a well structure 38 as described above in relation to the embodiments of FIGS. 1 and 2.

Figure 4:
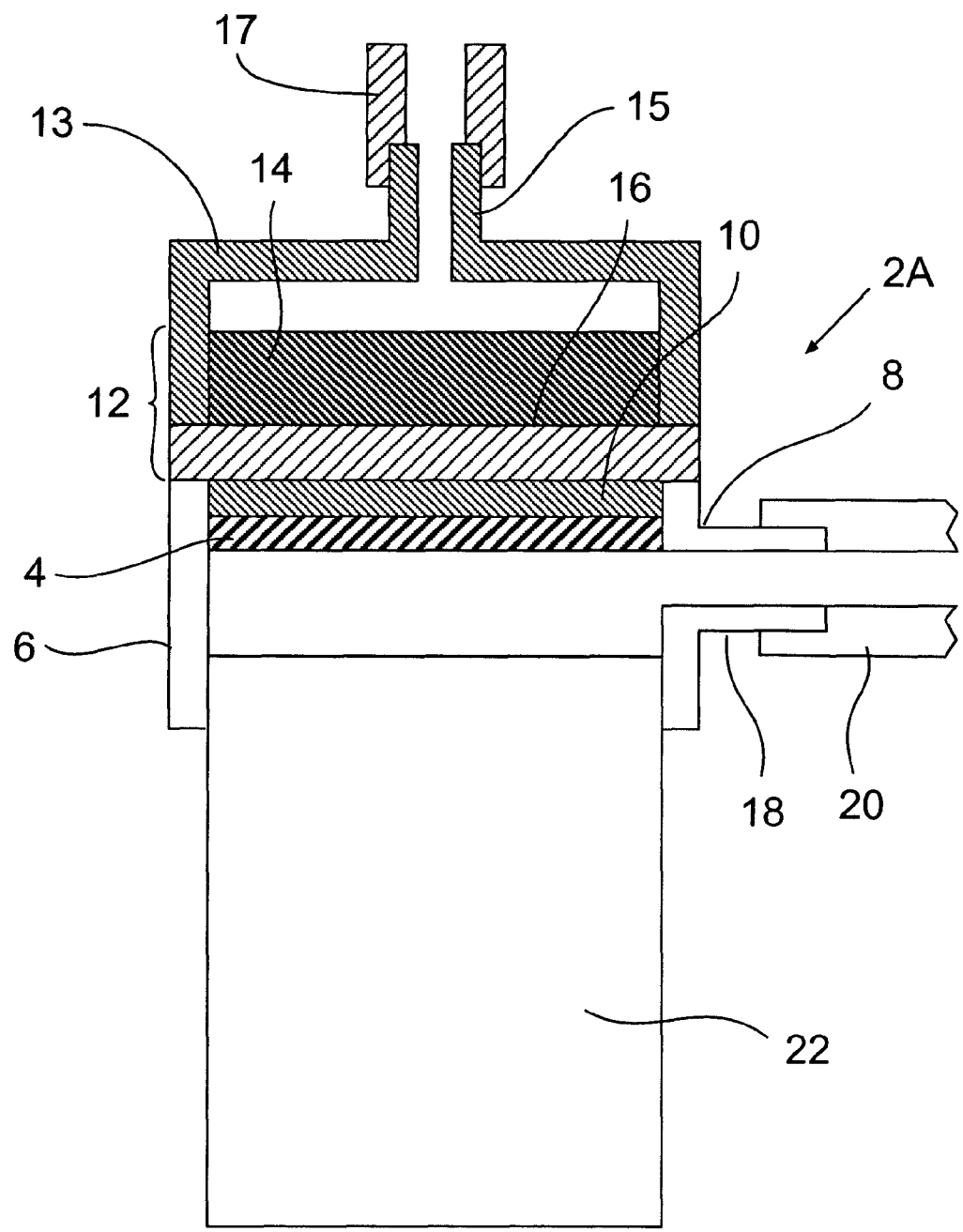
FIG. 4 shows a fourth embodiment of a device according to the present invention in cross-sectional view.

FIG. 4 shows a positive pressure system that may be used in the present invention. To the extent the elements are the same as those in FIGS. 1-3, the same reference numbers have been used.

As shown in FIG. 4, the device 2A is comprised of a porous support 4. Preferably the support is formed with an edge 6 or mounting piece that is designed to fit into or onto a manifold 8. One or more layers of a blotting membrane 10 (one shown) are placed on top of the support 4. A flow distributor 12 is then placed or mounted on top of the blotting membrane 10. The flow distributor may either have one or more wells 14 (one shown in this embodiment) attached to the top surface 16 of the flow distributor 12 or it may be a separate piece (not shown) which is simply attached or placed on top of the flow distributor 12. A positive pressure manifold or cover 13 is placed over and preferably removably secured to the wells 14 and/or flow distributor 12. The positive pressure manifold 13 has a port 15 connected to a source of positive pressure via tube 17. Positive pressure may come from a pump, a pressurized gas supply (tank, canister or the like) and other such well known sources used in the lab or industry.

As shown in FIG. 4, the manifold 8 is simply a collection manifold which has a port 18 that can be used to vent excess pressure. It may if desired contain an air filter to prevent the entrance of contaminants. The port 18 is located below the porous support 4. A waste collection device 22, in this instance, a receptacle, is mounted below the manifold or if desired in the manifold (not shown) to collect the liquid pulled through the device 2. Alternatively, the waste collection device can be a waste drain or other similar device as is known to one of ordinary skill in the art.

Various methods may be used in the present invention. The key factor being that they all rely on a vacuum or positive pressure driven filtration of the liquids rather than static diffusion as has occurred in the past.

The simplest method is to simply use the present invention to conduct one or more of the washing cycles. Typically each washing cycle is comprised of one or more washing steps. Generally, 2-5 steps are used per cycle.

Another method is to use the present invention in each step in which liquid needs to be removed from the blotting membrane such as after incubation of the antibodies or in the washing steps.

In all of these processes, any pressure suitable to move the liquid(s) through the device and into the manifold can be used. This can vary depending upon the membranes selected for blotting and the flow distributor, the manifold used, the desired speed of the filtration and the supply of vacuum or positive pressure available to the researcher.

Generally, the vacuum available may vary between 100 and 760 mm Hg (133 millibars and 1013 millibars). The use of valves, pressure restrictors and the like may also be used to keep the vacuum within the allowed ranges for the membranes used. A preferred vacuum manifold of one embodiment of the present invention is a STERICUP® device vacuum base and the use of a vacuum of about 100 mm Hg. Other suitable vacuum manifolds include but are not limited to the MULTISCREEN™ and MULTISCREEN$_{HTS}$ vacuum manifolds available from Millipore Corporation of Billerica, Mass.

Generally the positive pressure is supplied by an air line at pressures ranging from about 2 psi to about 15 psi. The use of valves, pressure restrictors and the like may also be used to keep the pressure within the allowed ranges for the membranes used. Such pressure systems include but are not limited to Amicon® stirred cell devices available from Millipore Corporation of Billerica, Mass. and positive pressure filtration units available from Caliper Life Sciences of Hopkinton, Mass.

Figure 5A:
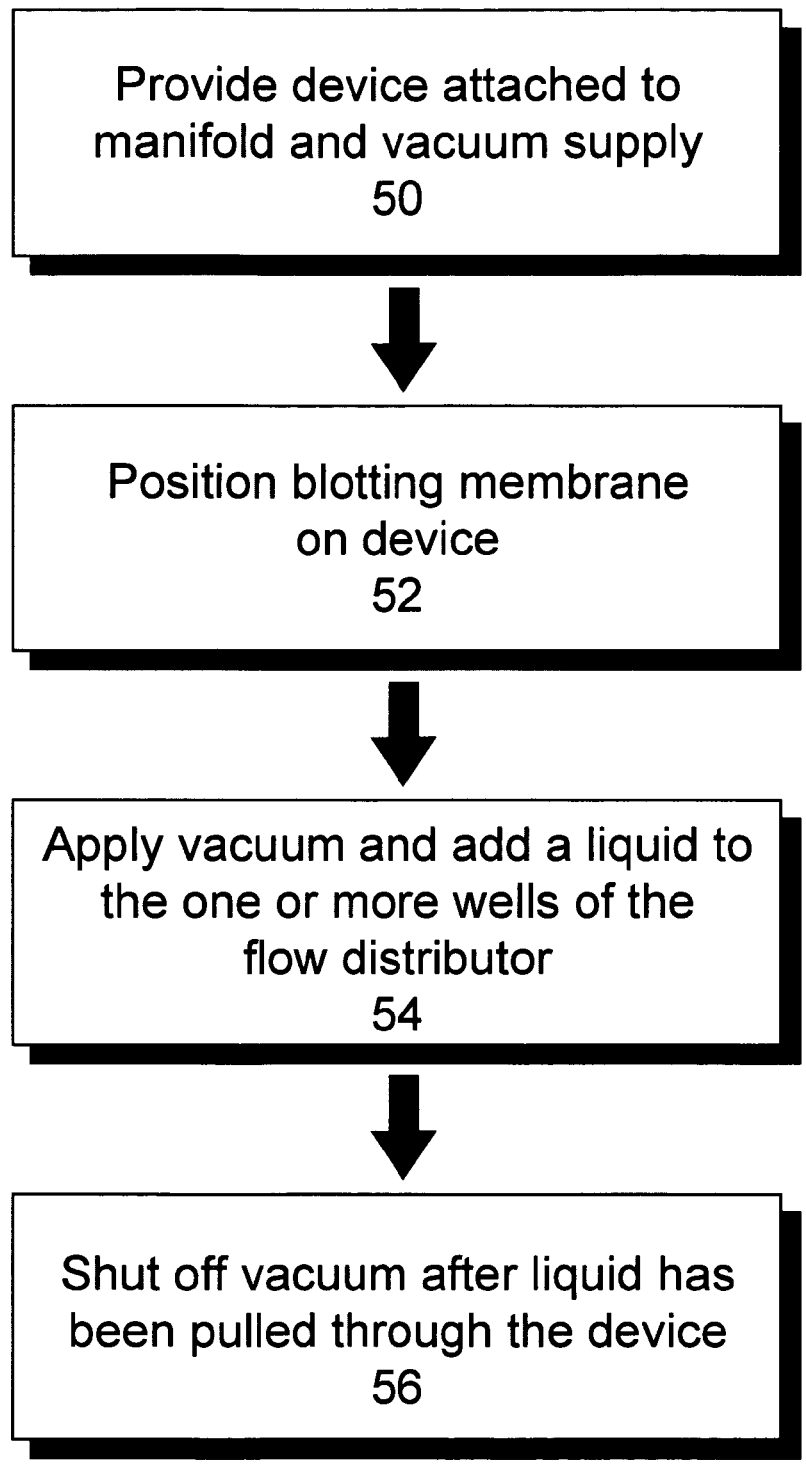
FIGS. 5A-5C show the embodiments of the process according to the present invention in block diagram form.
Figure 5B:
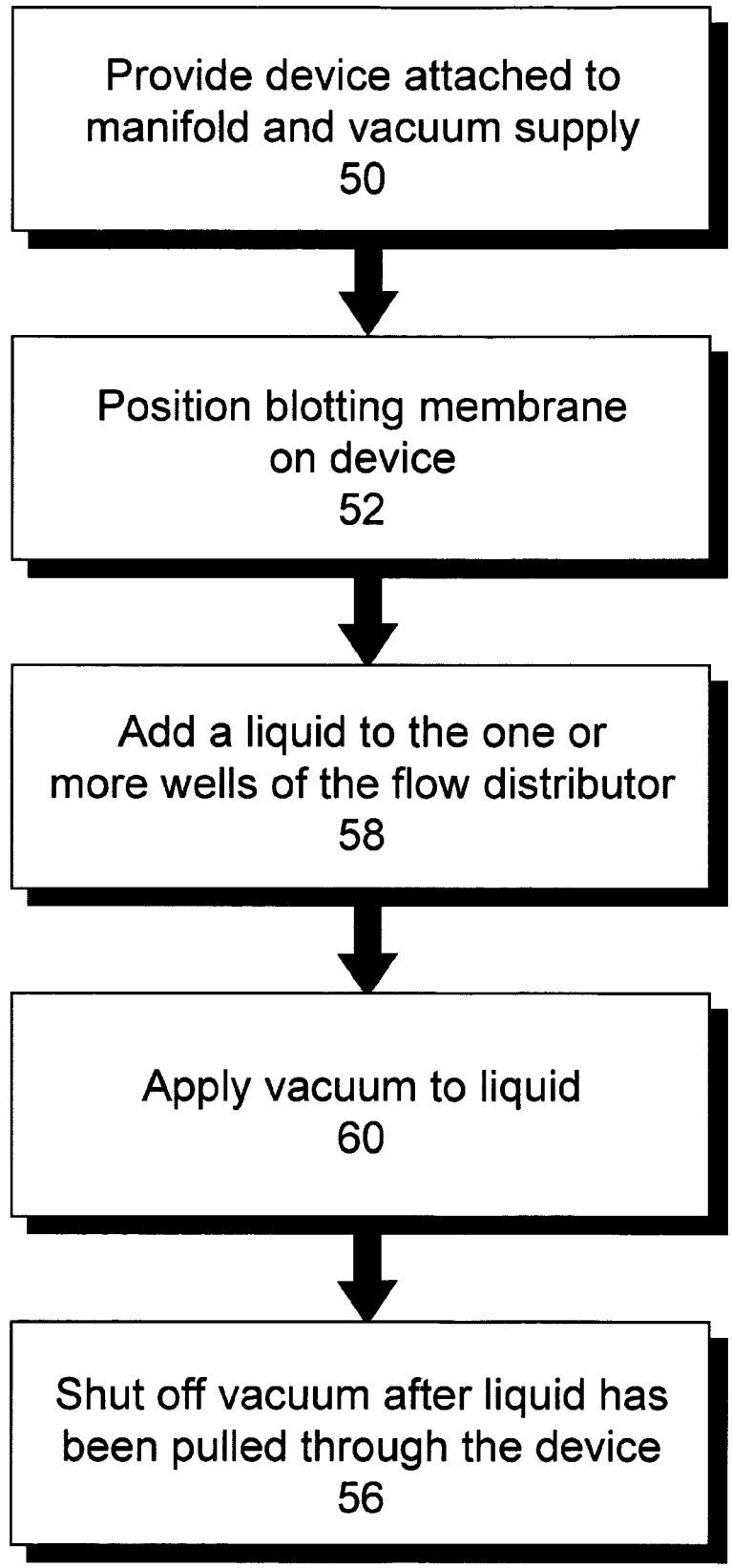
Figure 5C:
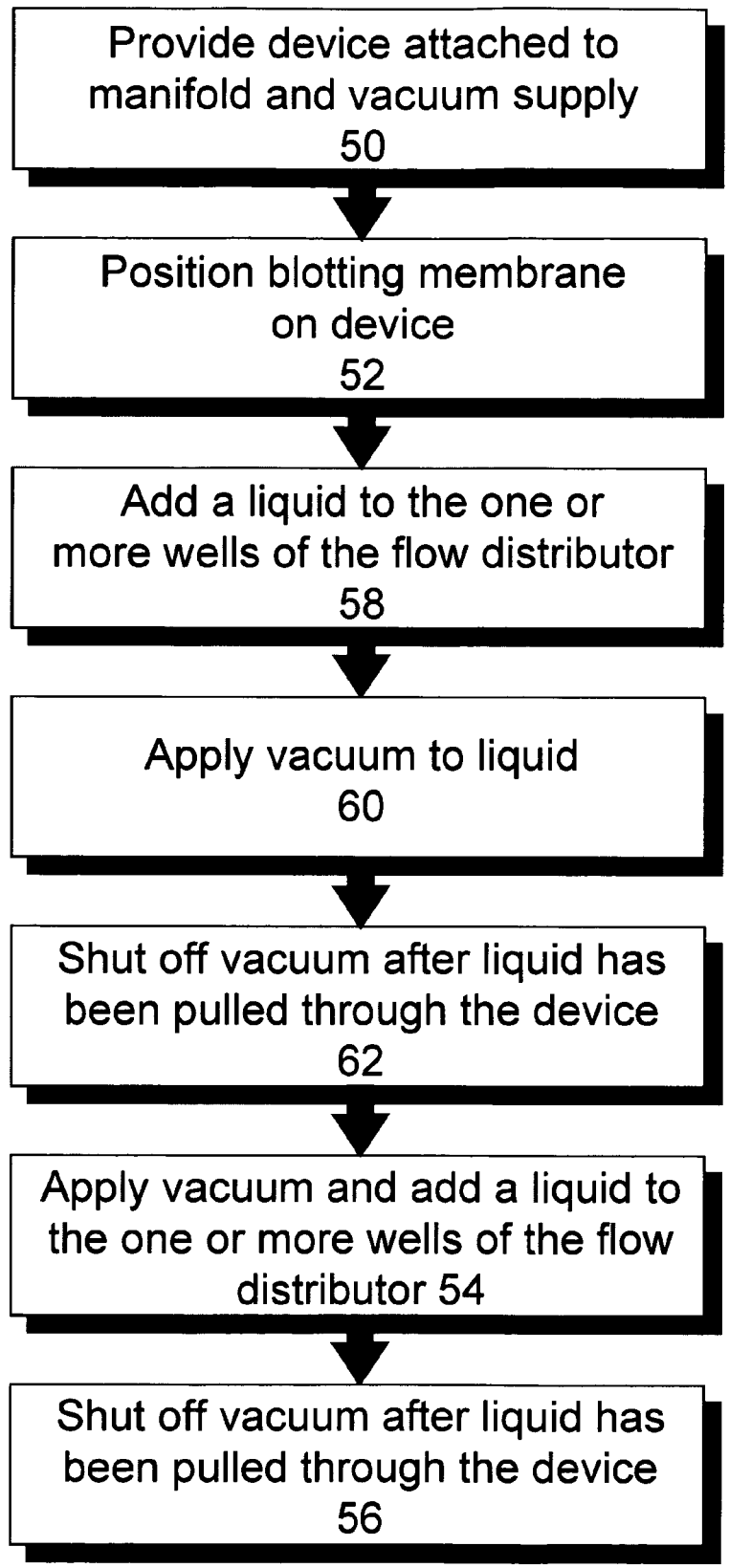

Typical processes are shown in FIGS. 5A-C in block diagram.

In FIG. 5A, a device according to the invention is provided and attached to a vacuum manifold and vacuum supply 50. The blotting membrane(s) are placed into the device in the proper position 52. Preferably the blotting membrane(s) in step 52 has been prewet (not shown). The vacuum is turned on and a liquid, such as with a wash liquid, is placed into the well(s) 54. The vacuum continues until the liquid has been drawn through the device and then the vacuum is turned off 56. When more than one blotting membrane is used, they can be arranged in series on top of each other and sufficient liquid containing the same desired reagents can be easily moved through the multiple layers in one process step. Generally when more than one layer is used it is preferred that one use between 2 and 10 layers, preferably between 2 and 5 layers at a time. Alternatively, one can use a flow distributor having multiple wells and use more than one blotting membrane in parallel to each other, each with their own well in the flow distributor and each with its own set of reagents as is required for its specific purpose. One can even use multiple layers in adjacent wells if desired.

In FIG. 5B, step 54 is eliminated and the liquid is added with the vacuum off 58 and allowed to incubate, such as may be required with the primary or secondary antibodies. The vacuum is then turned on in step 60.

In FIG. 55C, the steps of 55A and 55B are combined as sequential steps. Either or both steps may be repeated as needed or arranged in different sequences as desired to conduct the appropriate process.

Optionally, if one wishes, one can place a pan or single well device below the support of the membrane, preferably in the manifold itself. It can then be used to collect a single unbound reagent that may be expensive and which can be reused in future assays. Optionally, it may be subdivided into two or more subtrays.

Other processes may also be used with the device of the present invention.

Although the antibody concentrations used vary depending on the experimental design, 10-1,000 ng/mL is a typical range for standard method. Volumes of solution required are typically 0.1 mL/cm$^2$, 0.03 mL/cm$^2$ and 1.0 mL/cm$^2$ for blocking, antibody reactions and washing respectively.

The membrane contains, in its interstices, one or more substances to be detected. Generally these substances are present in the interstices either by virtue of having been blotted from a solid support for electrophoresis or chromatography or by direct application, usually to detect the presence, absence, or amount of a particular type of material such as an antibody or specific protein—i.e. a Dot-Blot type assay as described above. The definition of the membrane is not limited, however, to these instances, but applies to any case wherein one or more membranes contains in its interstices one or more substances to be detected. Included in the types of membranes envisioned for use in the present invention are membranes commonly used to blot electrophoresis gels such as nitrocellulose; nylon; or various other polymeric membranes, such as polyvinylidene fluoride (PVDF), sold as Immobilon™ membranes by Millipore Corporation of Billerica, Mass.

A variety of materials can be used to replicate the results of electrophoresis gels performed on various samples as is understood in the art. Most commonly, the samples contain biological substances such as individual proteins, antibodies, nucleic acids, oligonucleotides, complex carbohydrates, and the like, but the application of the technique is not limited to these substances. The invention technique is applicable to any membrane containing within it a substance to be detected regardless of the chemical composition of the membrane or of the target substances.

When membranes which represent replicas of electrophoretic results are employed, the transfer of the substances to be detected from the gel to the membrane can be conducted by utilizing membranes containing transfer buffer, by electroelution, electroblotting or by semi-dry blotting of the gels. Techniques for these transfers are well understood in the art, and do not constitute part of the invention herein.

The liquid to be supplied may contain detecting reagent or may simply be provided as a wash. The nature of the detecting reagent depends, of course, on the substance to be detected. Typically, proteins are detected by immunological reactions between antigen and antibody or immunoreactive portions thereof; typically the presence of nucleic acid fragments is detected by suitable oligonucleotide probes. The detecting substances responsible for the immediate or specific reaction with the substance to be detected may be further supplemented, if needed, with label and a multiplicity of applications of the detecting reagents may be needed—e.g., a protocol may include detection of an antigen by supplying an antibody labeled with an enzyme, e.g., commonly, horseradish peroxidase, and then this binding is detected by means of supplying substrate for this enzyme. In application of reagent, it is possible, though not preferred, to use only a positively pressed donor matrix to expose this component of the membrane for a defined period.

It is most convenient to conduct the method of the invention at room temperature, but elevated and lower temperatures can also be used. This can be affected by heating the device or its surrounding environment (as in a heat box or cooling box).

Blots can be sequentially analyzed with multiple antibodies or probes in the present device and process by stripping the previously bound antibodies from the blot followed by subsequent incubations with antibodies or other probes specific other target proteins. The stripping process disrupts the antigen-antibody bonds and dissolves the antibodies in the surrounding buffer. This is usually achieved by a combination of detergent and heat or by exposure to either high or low pH. The device, in combination with the flow distributor, enables the stripping of blots using the high or low pH method. The subsequent reprobing of blots either directly (e.g., using the same flow distributor used for striping) or subsequently after storage, would use the same protocol as the initial probing. Suitable kits for strip blotting are available from Chemicon International Inc under the brand names of ReBlot Plus kit (catalogue #2500), Re-Blot Plus-Mild solution (catalogue #2502) and Re-Blot Plus-Strong solution (catalogue #2504).

In standard western blotting, the antigen or target is transferred to one or more membranes support and probed with a suitable probe such as an antibody, protein (e.g., Protein A) or lectin (proteins or glycoproteins which binding to carbohydrate moieties). In some applications, a reverse format (e.g., reverse array) is used, wherein the antibody or other probes are spotted onto one or more membranes or other support (typically in an array format) and the antigen or target is presented to the immobilized antibodies on the array. Visualization of a target-probe binding event can be achieved by labeling of the antigens or targets or by using a secondary antibody specific for the target. Reverse arrays often employ mixtures of targets, for example lysates labeled with different fluorescent colors to enable parallel processing. Reverse assays can also be performed with the present invention.

EXAMPLE

The device of FIG. 1 was made using the base of a STERI-CUP® device (available from Millipore Corporation of Billerica, Mass.) as the vacuum manifold, a piece of Porex® porous plastic as the porous support, a Durapore® hydrophilic membrane (GVPP), 0.22 micron pore size as the flow distributor and a polystryrene strip (typically 4 mm larger than the membrane size. For example, 76 mm (L)×86 mm (W)×25 mm (H) for 72 mm×82 mm) well formed by bending the strip at 90° to form four corners and sealing the ends of the strip to each other using (3211 light cure adhesive, available from Loctite). The well was glued to the membrane surface using the Loctite 3211 light cure adhesive.

The base was connected to a valved vacuum line via its vacuum port.

A prewet (prewet in 100% methanol, then in water) blotting membrane (IMMOBILION™ Western blotting membrane available from Millipore Corporation of Billerica, Mass.) containing a sample of bovine liver lysate was placed on the base and all air bubbles between the base and membrane were removed. The flow distributor was placed on top of the blotting membrane. All air bubbles between the base and membrane were removed. A vacuum of 100 mm Hg was applied and then 10 mL of a blocking solution (1% casein in TBS-T (Tris buffered saline and Tween®-20 surfactant: 20 mM Tris-CL, pH7.6, 0.8% sodium chloride, 0.1% Tween®-20 surfactant) was added to the well. The vacuum was then shut off. 1 mL of a diluted rabbit anti-ERK primary antibody (diluted 1:2,000 with 1% casein in TBS-T) was added to the well and allowed to incubate for 10 minutes without any vacuum. A vacuum of 100 mm Hg was applied to filter the remaining antibody liquid. 30 mL of a TBS-T washing solution was added and filtered under vacuum. (until dryness). Three additional washes each, 30 mL of a TBS-T washing solution, were added sequentially and filtered under vacuum. The vacuum was then turned off and 1 mL of a diluted secondary antibody (alkaline phosphate conjugated goat anti-rabbit IgG antibody) (diluted 1:1,000 with 1% casein in TBS-T) was added to the well and allowed to incubate for 10 minutes without vacuum. The vacuum was then applied at 100 mm Hg to filter the remaining secondary antibody solution through the flow distributor. Four sequential washes each of 30 mL of a TBS-T washing solution were added and filtered under vacuum and then the vacuum was shut off. A substrate (Immobilon™ Western AP reagent) was added to the well and a detection. The membrane was exposed to an X-ray film for 1 minute and the film was processed by a film developer was completed.

Figure 6:
FIG. 6 shows the results of an example of a blot processed according to the prior art and the current invention.
Figure 6:
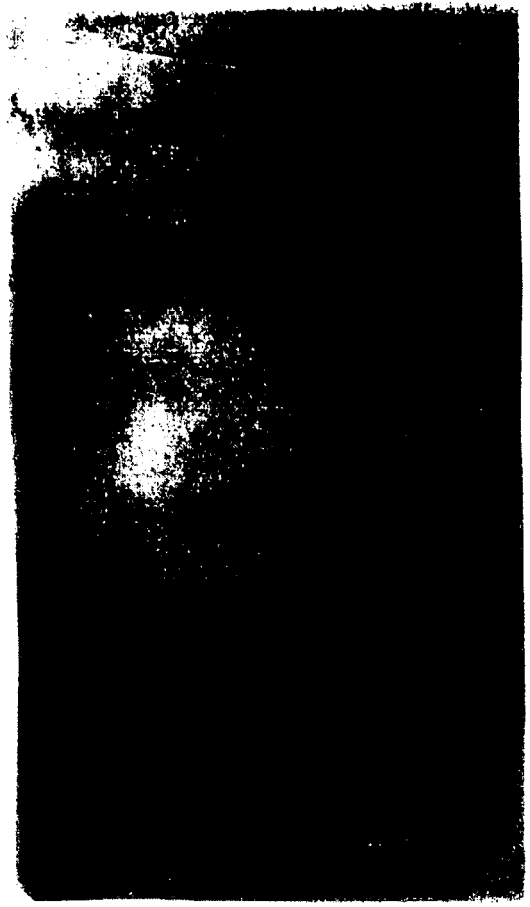

A comparative example using the traditional methodology and the same type of membrane, protein (ERK) and reagents was performed in over 3 hours of time.
1. Block the membrane in 1% casein/TBS-T for 1 h (0.1 mL/cm² membrane)
2. Add Anti-ERK antibody (1:10,000 dilution with 1% casein in TBS-T) for 1 h (0.1 mL/cm² membrane)
3. Wash four times for 5 minutes in TBS-T (1.0 mL/cm² membrane)
4. Add secondary antibody (anti-rabbit IgG alkaline phosphatase conjugated at 1:5,000 dilution with 1% casein in TBS-T) for 1 h (0.1 mL/cm² membrane)
5. Wash four times for 5 minutes in TBS-T (1.0 mL/cm² membrane)
6. Add Immobilon™ Western AP reagent and incubate for 5 minutes (0.05 mL/cm² membrane)
7. Expose to X-ray film for 1 minute then proceed to film development FIG. 6 shows the comparative example and the example according to the device and process of the present invention. The Figure demonstrates the high quality detection that can be achieved in only 30 minutes. In addition, the amount of antibodies used as compared to the traditional process was reduced by half in the process of the present invention in spite of the 5× increase in concentration in $\frac{1}{10}^{th}$ volume of the traditional example. This not only allows researchers to do more experiments but to do so with less reagents and higher quality results. Moreover, the background noise was significantly reduced as compared to the traditional method.

What we claim:

1. A process for conducting vacuum assisted immunoassays comprising the steps of:
   a. providing a vacuum manifold, a porous support placed on the vacuum manifold, the porous support has a device that is capable of fitting onto a vacuum manifold and wherein the device is selected from the group consisting of an edge and a mounting piece, one or more blotting membranes containing one or more biological entities to be assayed, the one or more blotting membranes being placed on the porous support, a flow distributor that is a plastic microporous hydrophilic membrane having has low protein binding characteristics to provide even liquid distribution over the one or more membranes supported on the porous support, the flow distributor being placed on top of the one or more blotting membranes and in contact with the one or more blotting membranes and one or more wells formed on a top surface of the flow distributor wherein each well has a separate flow distributor,
   b. removing any air bubbles from between the flow distributor and the one or more membranes,
   c. adding one or more reagents to the one or more wells and applying a vacuum to pull the reagents into the one or more membranes,
   d. adding one or more washing agents to the one or more we and applying a vacuum to pull the washing agents and any unbound reagents through the flow distributor, one or more membranes and porous support and into the vacuum manifold in order to conduct an immunoassay and
   e. detecting the one or more biological entities by applying a detection mechanism to the one or more wells and applying a vacuum to poll the detection mechanism through the flow distributor and into the one or more membranes.

2. The process of claim 1 wherein steps (c) and (d) are repeated one or more times.

3. The process of claim 1 wherein the step (e) of defecting the one or more biological entities by applying a detection mechanism selected from the group consisting of radiological entities and colorimetric entities to the one or more wells and applying a vacuum to pull the detection mechanism through the flow distributor and into the one or more membranes.

4. A process of passing a wash or reagent-containing liquid through one or more blotting membranes containing one or more biological entities, at least one of which is to be detected wherein the process comprises:
   a. providing a vacuum manifold, a porous support placed on the vacuum manifold, the porous support has a device that fits onto a vacuum manifold and wherein the device is selected from the group consisting of an edge and a mounting piece, a flow distributor that is a plastic microporous hydrophilic membrane having low protein binding characteristics to provide even liquid distribution over the one or more blotting membranes and one or more wells secured to a top surface of the flow distributor wherein each well has its own separate flow distributor,
b. placing the one or more blotting membranes containing the one or more biological entities on the porous support,
c. placing the flow distributor on top of the one or more blotting membranes and removing any air bubbles from between the flow distributor and the one or more blotting membranes,
d. placing the porous support, membranes and flow distributor with one or more wells into the manifold via the device that fits to the manifold,
e. adding a liquid to the well of the flow distributor, and
f. applying a vacuum to draw the liquid through the one or more blotting membranes.

5. A process of passing a wash or reagent-containing liquid through one or more layers of blotting membrane containing one or more biological entities, at least one of which is to be detected wherein the process comprises:
a. providing a device comprised of a collection manifold, a porous support, the porous support has a device that is capable of fitting onto the manifold and wherein the device is selected from the group consisting of an edge and a mounting piece, a flow distributor formed of a plastic microporous hydrophilic membrane having low protein binding characteristics to provide even liquid distribution over the one or more blotting membranes the flow distributor being in contact with the top of the blotting membranes, one or more wells formed on top of the flow distributor wherein each well has its own separate flow distributor and a positive pressure manifold removably attached to the top of the one or more wells, the cap having an inlet to its interior which inlet is connected to a supply of positive gas pressure,
b. placing the one or more layers of blotting membrane containing the one or more biological entities on the porous support,
c. placing the flow distributor on top of the one or more layers of blotting membrane and removing any air bubbles from between the flow distributor and the one or more blotting membranes, placing the support onto the manifold, adding a liquid to the one or more wells of the flow distributor, and
d. applying a positive pressure through the inlet to the positive pressure manifold to move the liquid from the wells through the flow distributor which provides even liquid distribution over the one or more layers of blotting membrane, through the one or more layers of blotting membrane and into the manifold.

\* \* \* \* \*

UNITED STATES PATENT AND TRADEMARK OFFICE
CERTIFICATE OF CORRECTION

PATENT NO.           : 8,557,600 B2                                               Page 1 of 1
APPLICATION NO.      : 11/582727
DATED                : October 15, 2013
INVENTOR(S)          : Masaharu Mabuchi et al.

It is certified that error appears in the above-identified patent and that said Letters Patent is hereby corrected as shown below:

In the Claims

In column 10, line 23, in claim 1 delete "has", therefor.

In column 10, line 37, in claim 1 delete "we" and insert -- wells --, therefor.

In column 10, line 45, in claim 1 delete "poll" and insert -- pull --, therefor.

In column 10, line 50, in claim 3 delete "defecting" an insert -- detecting --, therefor.

Signed and Sealed this
Eighteenth Day of March, 2014

Michelle K. Lee
*Deputy Director of the United States Patent and Trademark Office*